(12) United States Patent
Bradley et al.

(10) Patent No.: US 12,241,849 B2
(45) Date of Patent: Mar. 4, 2025

(54) METHODS OF DETERMINING PROTEIN OR PEPTIDE CONCENTRATION AND USES THEREOF

(71) Applicant: Eli Lilly and Company, Indianapolis, IN (US)

(72) Inventors: Scott Allan Bradley, Brownsburg, IN (US); William F. Weiss, IV, Indianapolis, IN (US); Wesley Clinton Jackson, Jr., Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1079 days.

(21) Appl. No.: 17/155,594

(22) Filed: Jan. 22, 2021

(65) Prior Publication Data

US 2021/0215625 A1   Jul. 15, 2021

Related U.S. Application Data

(63) Continuation of application No. PCT/US2019/046437, filed on Aug. 14, 2019.

(60) Provisional application No. 62/727,708, filed on Sep. 6, 2018, provisional application No. 62/720,607, filed on Aug. 21, 2018.

(51) Int. Cl.
| | |
|---|---|
| *G01N 24/08* | (2006.01) |
| *G01N 33/487* | (2006.01) |
| *G01N 33/68* | (2006.01) |
| *G01R 33/46* | (2006.01) |
| *G01R 33/465* | (2006.01) |

(52) U.S. Cl.
CPC ........... *G01N 24/08* (2013.01); *G01N 24/085* (2013.01); *G01N 24/088* (2013.01); *G01N 33/487* (2013.01); *G01N 33/6803* (2013.01); *G01R 33/4616* (2013.01); *G01R 33/465* (2013.01); *G01N 2496/00* (2013.01)

(58) Field of Classification Search
CPC .. G01N 24/08; G01N 33/6803; G01N 24/085; G01N 24/088; G01N 33/487; G01R 33/465; G01R 33/4616
USPC .......................................................... 436/173
See application file for complete search history.

(56) References Cited

U.S. PATENT DOCUMENTS

| | | | |
|---|---|---|---|
| 2014/0011727 A1* | 1/2014 | Shriver | G01N 33/9493 |
| | | | 530/350 |
| 2018/0169206 A1* | 6/2018 | Gerke | A61P 37/02 |
| 2019/0046627 A1* | 2/2019 | Álvarez Domínguez | ............ |
| | | | A61K 39/0011 |

FOREIGN PATENT DOCUMENTS

| | | |
|---|---|---|
| WO | 2000/26238 A2 | 5/2000 |
| WO | 2002/04523 A2 | 1/2002 |
| WO | 2003/014144 A2 | 2/2003 |
| WO | 2008/128228 A1 | 10/2008 |
| WO | 2016/179535 A1 | 11/2016 |

OTHER PUBLICATIONS

Neri, D. et al, Science 1992, 257, 1559-1563. (Year: 1992).*
Fong, S. et al, Journal of Molecular Biology 1998, 278, 417-429. (Year: 1998).*

(Continued)

*Primary Examiner* — Arlen Soderquist
(74) *Attorney, Agent, or Firm* — Michael R. Asam

(57) ABSTRACT

Methods for determining protein and/or peptide concentration or molecular parameter, such as the extinction coefficient, and uses thereof.

19 Claims, 11 Drawing Sheets

(56) References Cited

OTHER PUBLICATIONS

Whittington, S. J. et al, Biochemistry 2005, 44, 6269-6275. (Year: 2005).*
Wider, G. et al, Journal of the American Chemical Society 2006, 128, 2571-2576. (Year: 2006).*
Lim, W. K. et al, Proceedings of the National Academy of Sciences 2009, 106, 2595-2600. (Year: 2009).*
Chugh, J. et al, Archives of Biochemistry and Biophysics 2009, 481, 169-176. (Year: 2009).*
Lurie, D. J. et al, Comptes Rendus Physique 2010, 11, 136-148. (Year: 2010).*
Nodet, G. et al, Journal of the American Chemical Society 2009, 131, 17908-17918 with 6 pages of supporting information. (Year: 2009).*
Huang, T. et al, Talanta 2014, 125, 94-101. (Year: 2014).*
Monakhova, Y. B. et al, Journal of Pharmaceutical and Biomedical Analysis 2014, 100, 381-386. (Year: 2014).*
Webster, G. K. et al, Analytical Chemistry 2014, 86, 11474-11480. (Year: 2014).*
Josephs, R. D. et al, Trends in Analytical Chemistry 2018, 101, 108-119. (Year: 2018).*
Ravenscroft, N., International Conference Biological Beyond 2000, European Pharmacopeia, Strasbourg, 2000. 131-144. (Year: 2000).*
Cavaluzzi, M. J. et al, Analytical Biochemistry 2002, 308, 373-380. (Year: 2002).*
Holzgrabe, U. et al, Journal of Pharmaceutical and Biomedical Analysis 2005, 38, 806-812. (Year: 2005).*
Ravenscroft, N., et al, Bioanalysis 2010, 2, 343-361. (Year: 2010).*
Aubin, Y. et al, BioPharm International 2010, vol. 2010, Supplement, 9 pages. (Year: 2010).*
Barrere, C. et al, Journal of Magnetic Resonance 2012, 216, 201-208. (Year: 2012).*
Poppe, L. et al, Analytical Chemistry 2013, 85, 9623-9629. (Year: 2013).*
Rundlof, T. et al, Journal of Pharmaceutical and Biomedical Analysis 2014, 93, 111-117. (Year: 2014).*
Pauli, G. F. et al, Journal of Medicinal Chemistry 2014, 57, 9220-9231. (Year: 2014).*
Cutrone, J. Q. et al, Journal of Pharmaceutical and Biomedical Analysis 2017, 138, 166-174. (Year: 2017).*
Kiss, R. et al, Journal of Pharmaceutical and Biomedical Analysis 2018, 147, 367-377. (Year: 2018).*
Priscilla Kheddo et al, "Characterizing monoclonal antibody formulations in arginine glutamate solutions using 1 H NMR spectroscopy", MABS, vol. 8, No. 7, Sep. 2, 2016, pp. 1245-1258, XP055643123, US, ISSN: 1942-0862, DOI: 10.1080/19420862.2016.1214786.
Nuria Esturau et al, "Optimization of Diffusion-Filtered NMR Experiments for Selective Suppression of Residual Nondeuterated Solvent and Water Signals from 1 H NMR Spectra of Organic Compounds", Journal of Organic Chemistry, vol. 71, No. 11, May 1, 2006, pp. 4103-4110, XP055643117, US, ISSN: 0022-3263, DOI: 10.1021/jo060229i.
Leszek Poppe, et al, "Profiling Formulated Monoclonal Antibodies by 1 H NMR Spectroscopy", Analytical Chemistry, vol. 85, No. 20, Sep. 24, 2013, pp. 9623-9629, XP055643101, US, ISSN: 0003-2700, DOI: 10.1021/ac401867f.
Kang Chen, et al, "Simple NMR methods for evaluating higher order structures of monoclonal antibody therapeutics with quinary structure", Journal of Pharmaceutical and Biochemical Analysis, vol. 128, Sep. 1, 2016, pp. 398-497, XP055643098, Amsterdam, NL, ISSN: 0731-7085, DOI: 10.1016/j.jba.2016.06.007.
Olga B. Morozova, et al, "Reduction of Guanosyl Radicals in Reactions with Proteins Studied by Tr-CIDNP", Applied Magnetic Resonance, Springer Vienna, Vienna, vol. 44, No. 1-2, Oct. 12, 2012, pp. 233-245, XP035167227, ISSN: 1613-7507, DOI: 10.1007/S00723-012-0430-0.
Santosh Kumar Bharti, et al, "Quantitative 1H NMR spectroscopy", Trac Trends in Analytical Chemistry, vol. 35, May 1, 2012, pp. 5-26, XP055167863, ISSN: 0165-9936, DOI: 10.1016/j.trac.2012.02.007.
Scott A. Bradley, et al, "Measuring Protein Concentration by Diffusion-Filtered Quantitative Nuclear Magnetic Resonance Spectroscopy", Analytical Chemistry, vol. 91, No. 3, Jan. 4, 2019, pp. 1962-1967, XP055642882, US, ISSN: 0003-2700, DOI: 10.1021/acs.analchem.8b04283.

* cited by examiner

METHODS OF DETERMINING PROTEIN OR PEPTIDE CONCENTRATION AND USES THEREOF

The present invention relates to methods of determining concentration and/or molecular-specific parameters, such as the extinction coefficient, of a protein or peptide, and uses thereof.

The concentration of a peptide or protein, for example an antibody, in solution is an important property for the development and commercialization of biological therapeutics as well as in many other areas of research. For example, an accurate and precise concentration is required for determining the drug's efficacy and integrating data into a cohesive package for regulatory submission.

Presently, there exists several approaches for determining the concentration of a protein within a solution. One such approach involves determining molecule-specific parameters, such as the UV extinction coefficient (ε) or differential refractive index increment (dn/dc). Other approaches include (i) gravimetric analysis (Nozaki Y., Arch. Biochem. Biophys. 249 (2), 437-446 (1986)), (ii) chromogenic methods (Bradford M. M., Anal. Biochem. 72 (1-2), 248-254 (1976)), (iii) Kjeldahl nitrogen determination (Jaenicke L., Anal. Biochem. 61 (2), 623-627 (1974)), and (iv) amino acid analysis ("AAA") (Spackman D. H., et al., Anal. Chem. 30 (7): 1190-1206 (1958)). These methods, however, rely on experimentally derived properties of the protein such as ligand binding, degradation or derivitization as opposed to an intrinsic property of the protein, and can lead to inaccurate and imprecise results.

For example, with the UV extinction coefficient (ε) method, ε is predicted from empirical calculations; the result, however, is only an estimate and not the actual value (see e.g., Edelhoch H., Biochemistry 6(7), 1948-1954 (1967)). Moreover, gravimetric analysis of lyophilized proteins, for example, may contain a significant amount of bound water, salts and/or other formulation components that can lead to inaccurate concentration calculations. Chromogenic methods depend on the composition of the protein and require calibration curves to provide the absolute concentration. Issues and limitations also arise from the use of harsh conditions in the concentration determination performed by AAA, for example, that can cause degradation of several key amino acids during the hydrolysis and derivatization steps, long run times, and high variability. (Sittampalam G. S., et al, J. Assoc. of Official Anal. Chemists 71 (4), 833-838 (1988)). All of the above-noted issues lead to decreases in accuracy and precision when calculating concentration and molecular-specific parameters of proteins or peptides that can impact a molecule's efficacy, developability and commercialization.

Therefore, a new, accurate, absolute protein concentration method that is indifferent to the protein structure and formulation components, does not rely on molecular interactions or calibration curves to provide absolute concentrations, is more accurate and precise, and avoids harsh sample preparation is desired. Such method would be useful, for example, in determining the concentration of a protein or peptide in the preparation of the protein or peptide that is intended for a therapeutic use.

Nuclear magnetic resonance (NMR) spectroscopy is a quantitative technique that has been used to measure the concentration of compounds. However, the use of NMR spectroscopy for measuring absolute concentrations of large proteins in complex matrices, such as with therapeutic antibody formulations, is both challenging and presents issues similar to those noted above. For example, one challenge is that NMR spectra are dominated by intense peaks from various salts, buffers, surfactants, tonicity agents and even water present in therapeutic formulations. Another such issue is that the high-order structure of most proteins and antibodies creates unique magnetic environments around the hydrogen atoms that cause larger $^1$H chemical shift windows for a given amino acid. These issues, together with other inherent challenges posed by the use of NMR (e.g., inherently broader linewidths for protein resonances), lead to decreases in accuracy and precision when calculating concentration and molecular-specific parameters or proteins.

The present invention provides a novel quantitative nuclear magnetic resonance spectroscopy method for measuring absolute protein or peptide concentration. The qNMR spectroscopic method of the present invention produces clean spectra of the protein or peptide with well-resolved resonances, regardless of the solution complexity. The first step is to denature the protein (for a small peptide, this step is optional, but recommended) in order to decrease the linewidths of the protein resonances brought about by the secondary, tertiary, and quaternary structure and to enable integration. The second step is to acquire a qNMR spectrum with a diffusion filter to eliminate the resonances of water and the other formulation components. Finally, the data are compared to a reference standard for accurate concentration determination. This method is herein referred to as Method A. The concentration determined from Method A may then be used to determine a molecular parameter, such as the extinction coefficient, of the protein or peptide.

The present invention therefore provides a method of obtaining the concentration of a protein in solution, wherein the method comprises denaturing the protein, performing NMR spectroscopy with a diffusion filter, and calculating the concentration of the protein using a reference standard. The present invention also provides a method of obtaining the concentration of a peptide in solution, wherein the method comprises performing NMR spectroscopy with a diffusion filter, and calculating the concentration of the peptide using a reference standard. In some embodiments, the method further comprises denaturing the peptide prior to performing NMR spectroscopy with a diffusion filter.

The present invention provides a method of obtaining the extinction coefficient of a protein in solution, wherein the extinction coefficient is determined by the Beer-Lambert Law, and wherein the protein concentration used in the Beer-Lambert Law is determined in a method comprising denaturing the protein, performing NMR spectroscopy with a diffusion filter, and calculating the concentration of the protein using a reference standard.

The present invention also provides a method of obtaining the extinction coefficient of a peptide in solution, wherein the extinction coefficient is determined by the Beer-Lambert Law, and wherein the peptide concentration used in the Beer-Lambert Law is determined in a method comprising an optional step of denaturing the peptide, followed by the steps of performing NMR spectroscopy with a diffusion filter and calculating the concentration of the protein using a reference standard. In some embodiments, the method comprises denaturing the peptide prior to performing NMR spectroscopy with a diffusion filter.

The present invention provides a method of determining the concentration of a protein in the preparation of a drug substance or drug product, wherein the substance comprises the protein in solution, and wherein the method comprises obtaining a molecular parameter of the protein. In some embodiments, the molecular parameter is the extinction coefficient, and the extinction coefficient is determined by the Beer-Lambert Law, and the protein concentration used in the Beer-Lambert Law is determined in a method comprising denaturing the protein, performing NMR spectroscopy with a diffusion filter, and calculating the concentration of the protein using a reference standard.

The present invention provides a method of determining the concentration of a peptide in the preparation a drug substance or drug product, wherein the substance comprises the peptide in solution, and wherein the method comprises obtaining a molecular parameter of the peptide. In some embodiments, the molecular parameter is the extinction coefficient, and the extinction coefficient is determined by the Beer-Lambert Law, and the peptide concentration used in the Beer-Lambert Law is determined in a method comprising optionally denaturing the peptide, performing NMR spectroscopy with a diffusion filter, and calculating the concentration of the peptide using a reference standard. In some embodiments, the method comprises denaturing the peptide prior to performing NMR spectroscopy with a diffusion filter.

The present invention further provides a method of obtaining a molecular parameter of a protein in solution, wherein the method comprises denaturing the protein, performing NMR spectroscopy with a diffusion filter, calculating the concentration of the protein using a reference standard, and determining the molecular parameter of the protein from the calculated concentration. In an embodiment, the calculated concentration of the protein and a determined system property is used in a corresponding equation to determine the molecular parameter of the protein. In some embodiments, the molecular parameter is the extinction coefficient and the corresponding equation is the Beer-Lambert law.

The present invention also provides a method of obtaining a molecular parameter of a peptide in solution, wherein the method comprises optionally denaturing the peptide, and then performing NMR spectroscopy with a diffusion filter, calculating the concentration of the peptide using a reference standard, and determining the molecular parameter of the protein from the calculated concentration. In an embodiment, the calculated concentration of the peptide and a determined system property is used in a corresponding equation to determine the molecular parameter of the peptide. In some embodiments, the molecular parameter is the extinction coefficient and the corresponding equation is the Beer-Lambert law.

The present invention provides a method of determining a dose in the preparation of a drug substance or drug product, wherein the substance comprises a protein in solution, wherein the method comprises obtaining a molecular parameter of a protein from a reference batch, wherein the molecular parameter is determined in a method comprising denaturing the protein, performing NMR spectroscopy with a diffusion filter, calculating the concentration of the protein using a reference standard, and determining the molecular parameter of the protein from the calculated concentration. In a further embodiment, the method comprises preparing a test batch of drug substance or drug product, wherein said concentration of the protein in the test batch is determined from the molecular parameter. In some such embodiments, the protein concentration is determined using, in the corresponding equation, the molecular parameter and a corresponding system property.

The present invention provides a method of determining a dose in the preparation of a drug substance or drug product, wherein the substance comprises a peptide in solution, wherein the method comprises obtaining a molecular parameter of the peptide from a reference batch, wherein the molecular parameter is determined in a method comprising optionally denaturing the peptide, performing NMR spectroscopy with a diffusion filter, calculating the concentration of the peptide using a reference standard, and determining the molecular parameter of the peptide from the calculated concentration. In a further embodiment, the method comprises preparing a test batch of drug substance or drug product, wherein said concentration of the peptide in the test batch is determined from the molecular parameter. In some such embodiments, the peptide concentration is determined using, in the corresponding equation, the molecular parameter and a corresponding system property.

The present invention also provides a method of determining the concentration of a protein or peptide in the preparation of a reference batch, wherein the reference batch comprises the protein or peptide in solution, and wherein the method comprises denaturing the protein or optionally denaturing the peptide, performing qNMR spectroscopy with a diffusion filter, calculating the concentration of the protein or peptide using a reference standard and a referencing technique, and determining the molecular parameter of the protein or peptide from the calculated concentration. In a further embodiment, the method further comprises determining the concentration of a protein or peptide in the preparation a test batch, wherein said concentration of peptide or protein in the test batch is determined from the molecular parameter.

The present invention provides embodiments that are applicable to the methods described herein. One such embodiment comprises a method wherein the protein or peptide is denatured with a chaotropic agent. In some such embodiments, the chaotropic agent is urea-$d_4$. In other such embodiments, the chaotropic agent is guanidinium chloride-$d_6$. In some embodiments, the reference standard is an internal reference standard. In preferred embodiments, the reference standard is an external reference standard. In some such embodiments, the external reference standard is a small-molecule primary standard. In a particular embodiment, the external reference standard is maleic acid. In some such embodiments, the external referencing technique is PULCON. In some embodiments, the protein is an antibody. In some such embodiments, the antibody is a monoclonal antibody. In other such embodiments, the antibody is a bispecific antibody. In some embodiments, the solution comprising the protein or peptide being measured comprises $D_2O$.

The present invention also contemplates the use of Method A, or the molecular parameter determined from the concentration obtained in Method A, in a variety of applications. Such applications include determining a toxicology, clinical, and/or commercial drug product dose, a method of determining corporate or primary reference standards, a method of determining the concentration of protein or peptide during manufacturing, a method of aliquoting a protein or peptide, a method of aliquoting a protein or peptide wherein the concentration of aliquoted protein or peptide is similar to the desired concentration, a method comprising a test at lot release, or a method of formulating a drug substance or drug product.

The present invention contemplates that Method A may be used for purposes described herein pertaining to any protein or peptide, such as proteins or peptides in the areas of therapeutics or oil. By way of example (not intended to be limiting), Method A may be implemented in applications relating to any or all of the following, including any such biosimilars thereof, wherein the protein or peptide is the active ingredient in the following or any such biosimilars of the following: dulaglutide (sold in some countries under the name Trulicity®), ixekizumab (sold in some countries under the name Taltz®), ramucirumab (sold in some countries under the name Cyramza®), cetuximab (sold in some countries under the name Erbitux®), olaratumab (sold in some countries under the name Lartruvo®), necitumumab (sold in some countries under the name Portrazza®), anti-CGRP antibodies such as galcanezumab (also known as LY2951742), anti-IL-23 antibodies such as mirikizumab (also known as LY3074828), solanezumab (also known as LY2062430), tanezumab, anti-N3pG-Aβ antibodies, anti-Tau antibodies, anti-Aβ42 antibodies, anti-BAFF/IL-17 bispecific antibodies, anti-CSF-1R antibodies, anti-CXCR1/2 antibodies, anti-IL-21 antibodies, anti-IL-23/CGRP bispecific antibodies, anti-IL-33 antibodies, anti-PD-L1 antibodies, and anti-TIM-3 antibodies.

The present invention also contemplates that Method A (i) is suited to serve as the basis for measuring other intrinsic parameters of a protein or peptide or converting any of the current relative concentration methods into an absolute method, (ii) may be used to quantitate peptides that lack chromophoric amino acids and are difficult to monitor by UV, (iii) allows for sample preparation and data acquisition that is easier, quicker, and safer than the current AAA method, (iv) provides linearity, precision, and accuracy of the resulting concentrations that are suitable for a variety of proteins and formulations, and (v) may be used to quantitate other types of macromolecules (e.g., polymers, surfactants, etc.) in the presence of small-molecule contaminants.

The present invention contemplates that the methods described herein can utilize the mathematical equations also described herein. For example, the protein concentration, $c_P$, in units of grams per liter can be calculated from the qNMR spectrum with the following equation $$c_P = c_S \frac{A_P H_S}{A_S H_P} f_{DF} \; f_{ER} \; f_{DIL} \; f_U. \quad \text{(Eq. 1)}$$

A detailed description of this equation, for example, is described herein.

A person of ordinary skill would recognize that although particular software programs are exemplified herein, other programs may be used to obtain comparable results.

BRIEF DESCRIPTION OF THE DRAWINGS

FIG. 3A: NMR spectra of the denature mAb standard acquired with the bppste pulse sequence. Inset: expansion of the peak for the I/L/V resonances. Inset: magnified image of indicated region. FIG. 3B: Left: the pure NMR spectra for the different diffusing species as determined by the DECRA algorithm. Right: Stejkal-Tanner plot and diffusion coefficients from the DECRA algorithm.

FIG. 4A: Representative data from the $T_1$ and $T_2$ measurements using the bppste pulse sequence. Left: NMR spectra from and parameters for the bppste pulse sequence setup to measuring $T_1$. Right: NMR spectra from and parameters for the bppste pulse sequence setup to measuring $T_2$. FIG. 4B: Plot for $T_1$ and $T_2$ calculations.

DEFINITIONS

Figure 1:
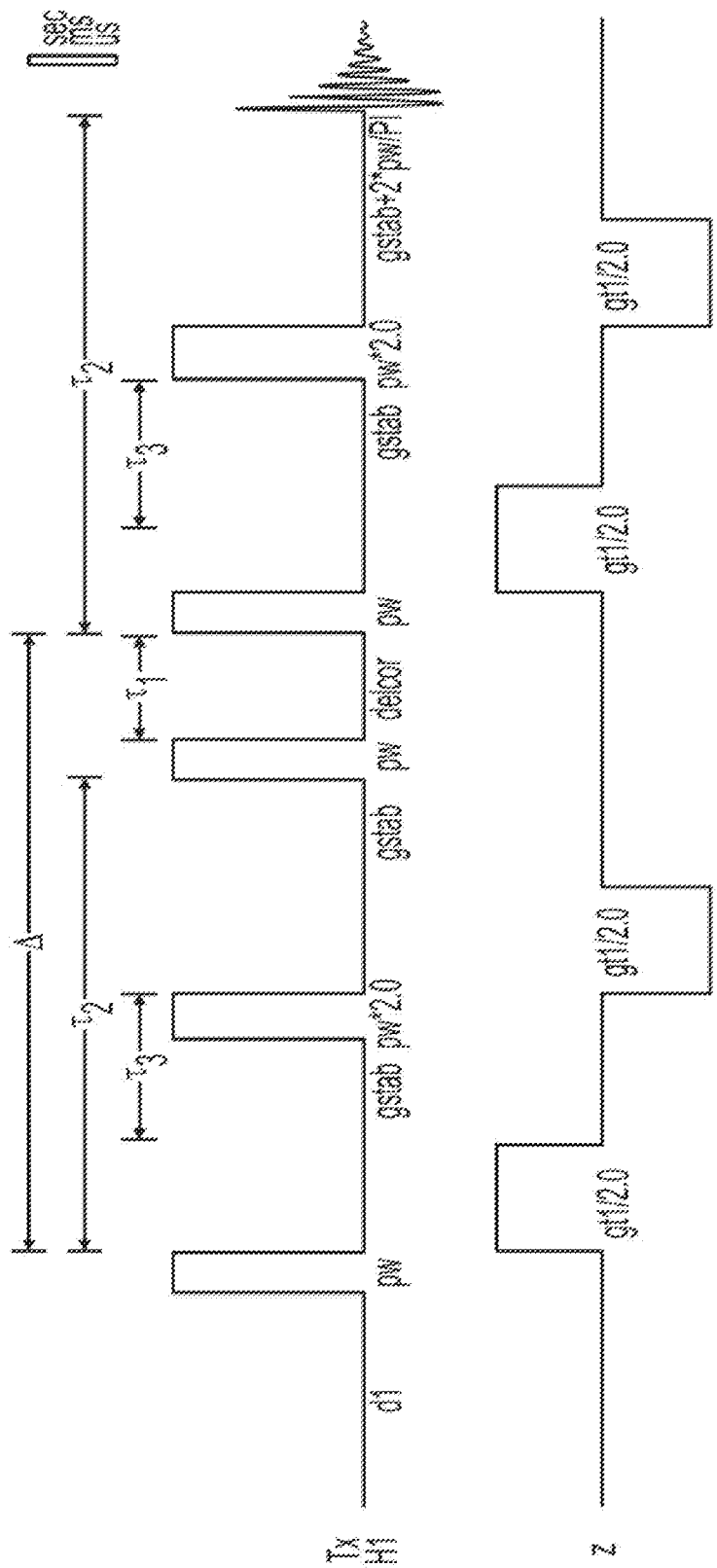
FIG. 1. The bppste pulse sequence for Agilent (a.k.a., Dbppste) spectrometers and definition of the various delays.

As used herein, "nuclear magnetic resonance spectroscopy" (also referred to as "NMR spectroscopy") refers to a spectroscopic technique known to one of ordinary skill in the art, in which nuclear magnetic resonance (NMR) spectra can be used to study the structure of organic molecules. As used herein, "quantitative nuclear magnetic resonance spectroscopy" (also referred to as "qNMR spectroscopy") refers to obtaining quantitative information about sample purity or concentration from one or more NMR spectra. Such spectra are herein referred to as quantitative nuclear magnetic resonance (qNMR) spectra. NMR spectroscopy may incorporate the use of a "diffusion filter," which can be used to selectively dampen the signal of smaller molecules in a mixture based on their size (see e.g., Stilbs P., Prog. Nucl. Magn. Reson. Spectrosc. 19(1): 1-45 (1987)). To balance the attenuation of the matrix peaks and protein peaks, the strength of the diffusion filter can be determined by a person of ordinary skill based on the context of each experiment. For example, if the balance is too weak, then the diffusion filter has limited value. If the balance is too strong, the diffusion filter begins to suppress the protein signals, which reduces the signal-to-noise ratio of the measurement. This reduction may then result in longer experiment times. As another example, if one of the matrix components is not completely eliminated and it presents an interfering peak, then there will be a contribution to the protein peak area, and it must be subtracted in order to get the most accurate results. This can be done by preparing a blank sample containing the matrix without the protein, running the blank sample with the diffusion filter, determining the area of the remaining matrix peak, and subtracting this number from the area obtained for the protein sample.

As used herein, a "reference standard" refers to a compound whose $^1$H-NMR spectrum provides at least one distinctive peak representing a known number of protons, and whose purity and concentration is known with a high degree of certainty. A reference standard may be an internal reference standard, wherein the reference standard is present in the solution containing the protein or peptide of interest, or a reference standard may be external, wherein the reference standard is separate from the solution containing the protein or peptide of interest. A reference standard may be a small-molecule primary reference standard, which is a material that is not calibrated against another standard and instead is defined by qualities such as its mass. Small molecule certified reference materials commonly used as $^1$H qNMR internal standards are readily available and may also be used as external standards [see e.g., Rigger et al., M. J. AOAC International, 2017, 100, 1365-1375.].

A referencing technique is a mathematical algorithm that uses data of the reference standard. For example, an external referencing technique is the mathematical algorithm that uses data of the external reference standard. One example of such is the pulse length-base concentration determination (PULCON) technique (Wider G. and Dreier L. J., Am. Chem. Soc. 128(8), 2571-2576 (2006)).

As used herein, "DF-qNMR" spectra refer to NMR spectra to which a diffusion filter has been applied, and from which quantitative information about the purity or concentration of the protein or peptide of interest can be obtained when compared to a reference standard.

As used herein, a "molecular parameter" means a scalar value that relates the way that some system property (e.g. absorbance, density, refractive index) changes in response to changes in other system properties (e.g. temperature, pressure, or composition). The equation ("corresponding equation") used to determine a molecular parameter may vary depending on what system property or properties are known. A molecular parameter refers to an intrinsic property of a protein or peptide.

For example, an extinction coefficient ($\varepsilon$) is a molecular parameter that describes how the absorbance of a solution changes in response to changes in the concentration of the absorbing species and the pathlength through which the light travels. The extinction coefficient of a protein or peptide [mL/(mg·cm)] can be determined by a combination of ultraviolet-visible (UV-Vis) spectroscopy and Method A as follows: $A=\varepsilon c l$ (Beer-Lambert Law), wherein A is the absorbance of the protein or peptide solution, l is the pathlength [cm], and c is the absolute protein or peptide concentration [mg/mL]. As another example, the apparent partial specific volume ($\bar{v}$) [mL/g] of a protein or peptide can be determined by a combination of densitometry and Method A as follows: $\rho=\rho_0+(1-\bar{v}\rho_0)(c/1000)$, wherein $\rho$ is the density of the protein or peptide solution [g/mL], $\pi_0$ is the density of the protein or peptide solution matrix [g/mL], and c is the absolute protein or peptide concentration [mg/mL]. As a third example, the (differential) refractive index increment (dn/dc) of a protein or peptide [mL/mg] can be determined by a combination of (differential) refractometry and Method A as follows: $n=n_0+(dn/dc)c$, wherein n is the refractive index of the protein or peptide solution, $n_o$ is the refractive index of the protein or peptide solution matrix, and c is the absolute protein or peptide concentration [mg/mL].

A person of ordinary skill can determine the molecular parameter of interest by linear regression of multiple measurements of absorbance/density/refractive index as a function of concentration (concentration as determined from Method A). A molecular parameter, such as the extinction coefficient, may be used to determine the concentration of a medicament by measuring the corresponding system property, such as UV absorbance, and solving the corresponding equation that correlates them (e.g., Beer-Lambert Law).

The general structure of a "monoclonal antibody" is known. An IgG antibody is hetero-tetramer of four polypeptide chains (two identical "heavy" chains and two identical "light" chains) that are cross-linked via intra- and inter-chain disulfide bonds. The variable regions of each heavy chain-light chain pair associate to form binding sites. The heavy chain variable region ($V_H$) and the light chain variable region ($V_L$) can be subdivided into regions of hypervariability, termed complementarity determining regions ("CDRs"), interspersed with regions that are more conserved, termed framework regions ("FR"). Each $V_H$ and $V_L$ is composed of three CDRs and four FRs, arranged from amino-terminus to carboxy-terminus in the following order: FR1, CDR1, FR2, CDR2, FR3, CDR3, FR4. The CDRs contain most of the residues which form specific interactions with the antigen.

As used herein, "bispecific antibody" refers to a bivalent antibody construct that includes, but is not limited to, an IgG-scFv format (as reported in PCT/US2015/058719) and bivalent IgG formats (as disclosed in US 2018/0009908). The present invention also contemplates that any human-engineered protein or antibody, regardless of tertiary or quaternary structure, may also be used in the methods described herein. Examples of such human-engineered proteins or antibodies include trispecific or tetraspecific antibodies and fusion proteins.

As used herein, a peptide comprises a polymeric chain of amino acids. These amino acids can be natural or synthetic amino acids, including modified amino acids. Peptides may have less secondary and tertiary structure, but are prone to aggregate in solution; therefore, a peptide may also be denatured with a chaotropic agent. Denaturation of a peptide may result in an increase in the signal-to-noise ratio in NMR spectroscopy, thereby making integration easier. Denaturing a peptide might also allow for the examination of more concentrated samples, thereby leading to shorter experimental times. For the purposes of the methods described herein, the determination of the peptide concentration may be more accurate when the peptide is denatured. For denaturing with a chaotropic agent, the preferred chaotropic agent will depend on the particular requirements of each peptide and can be determined experimentally by a person of ordinary skill in the art.

A person of ordinary skill in the art would recognize that a protein comprises one or more polymeric peptide chains of amino acids. These amino acids can be natural or synthetic amino acids, including modified amino acids. A protein may be a recombinant protein. A protein's primary structure is comprised of its linear sequence of monomeric amino acid subunits. A protein's secondary structure includes the pattern of hydrogen bonds giving rise to three-dimensional structural features of local segments of the amino acid chain, such as a-helices and B-sheets. A protein's tertiary structure describes the overall shape of a protein as defined by the three-dimensional atomic coordinates. Quaternary structure refers to the arrangement of two or more protein subunits in a complex. A protein can be "denatured," wherein an external stress or chaotropic agent is added to the solution containing the protein and the protein becomes unfolded. A denatured protein therefore has lost the majority of its secondary, tertiary, and quaternary structural features. Examples of chaotropic agents include urea-$d_4$ and guanidinium chloride-$d_6$.

Also used herein, a "solution" refers to a peptide or protein in a human-engineered aqueous mixture that contains components in addition to water. A "batch" refers to a specific quantity of a drug or other material that is a protein or peptide and is intended to have uniform character and quality, within specified limits, and is produced according to a single manufacturing order during the same cycle of manufacture. A "lot" refers to a batch, or a specific identified portion of a batch, having uniform character and quality within specified limits; or, in the case of a drug product produced by continuous process, it is a specific identified amount produced in a unit of time or quantity in a manner that assures its having uniform character and quality within specified limits. A "reference batch" refers to established and appropriately characterized in-house primary reference material, wherein the material comprises a protein or peptide, and wherein the material is prepared from lot(s) representative of production and clinical materials. Method A is used to determine the concentration and molecular parameter, such as the extinction coefficient, of a protein or peptide in solution in the reference batch. The molecular parameter, such as the extinction coefficient, obtained from the reference batch, is then used to determine the concentration of protein or peptide in a subsequent lot (herein referred to as a "test batch").

As used herein "drug product" is a finished dosage form, e.g., tablet, capsule, or solution, that contains a drug substance, generally, but not necessarily, in association with one or more other ingredients. A "drug substance" is an active ingredient that is intended to furnish pharmacological activity or other direct effect in the diagnosis, cure, mitigation, treatment, or prevention of disease or to affect the structure or any function of the human body, but does not include intermediates used in the synthesis of such ingredient. As used herein, a drug substance comprises a protein or peptide. Method A may be used for various purposes related to drug product or drug substance comprising a protein or peptide, such as throughout manufacturing of the drug product or drug substance.

A "dose" refers to an amount of protein or peptide in the matrix that will elicit the desired biological or medical response. The substance may be lyophilized or in an aqueous solution. To prepare a substance intended for a therapeutic use, a person of skill in the art would appreciate that an accurate and precise concentration of the protein or peptide is required. The methods described herein provide a novel means of obtaining the protein or peptide concentration by determining the extinction coefficient or other molecular parameter of the protein or peptide in a reference batch and then using this extinction coefficient or other molecular parameter to determine the concentration of protein or peptide in subsequent test batches.

To aliquot means removing a portion of a larger volume in one vessel and adding it into a separate vessel. A vessel can be any item, such as a container, vial, flask, or device, that is suitable to hold a protein or peptide, lyophilized or in solution.

A test at lot release refers to an appropriate laboratory determination of satisfactory conformance to final specifications for the drug product (comprising a protein or peptide), including the strength (concentration) of each active ingredient, prior to release (release by the manufacturer onto the market). The test at lot release may be, for example, a UV test at lot release. The concentration of the protein or peptide may be determined from the protein or peptide's extinction coefficient, wherein the extinction coefficient is determined from Method A in a reference batch.

The following Examples further illustrate the invention and provide typical methods and procedures for carrying out various particular embodiments of the present invention. However, it is understood that the Examples are set forth the by way of illustration and not limitation, and that various modifications may be made by one of ordinary skill in the art.

EXAMPLES

Preparation of Samples

Reference standard: Any compound with a $^1$H-NMR spectrum that provides at least one distinctive peak representing a known number of protons, known purity and concentration with a high degree of certainty, and chemical and physical stability in solution may be used to facilitate the calculation of the absolute concentration from the DF-qNMR spectra. For example, maleic acid may be used as an external quantitation reference standard. To prepare the maleic acid as an external reference standard, certified maleic acid (11.183 mg, 0.096347 mmol) is placed in a 5 mL volumetric flask and dissolved in $D_2O$. An aliquot is transferred to a tube, such as a Wilmad 435 precision 4 mm NMR tube, such that the sample height is 40 mm.

Protein Samples: Guanidinium chloride-$d_6$ (0.6 g, 6 mmol) is placed in a 1 mL volumetric flask. The flask is placed onto a balance, and 400 µL of protein solution is added. The solution is then gently sonicated and vortexed until all solids are dissolved. $D_2O$ is added to achieve the final volume. An aliquot is transferred to a tube, such as a Wilmad 435 precision 4 mm NMR tube, such that the sample height in the tube is 40 mm.

Peptide Samples: Urea-$d_4$ (0.13 g, 2 mmol) is placed in a 1 mL volumetric flask. The flask is placed onto a balance, and ~1 mL of protein solution is added. The solution is then gently sonicated and vortexed until all solids are dissolved. $D_2O$ is added to achieve the final volume. An aliquot is transferred to a tube, such as a Wilmad 435 precision 4 mm NMR tube, such that the sample height in the tube is 40 mm.

Calculations

The protein concentration, $c_P$, in units of grams per liter is calculated from the DF-qNMR spectrum with the following equation $$c_P = c_S \frac{A_P H_S}{A_S H_P} f_{DF} \; f_{ER} \; f_{DIL} \; f_U \qquad \text{(Eq. 1)}$$

where $c_S$ is the concentration of the reference standard, $A_P$ is the area of the selected protein peak in the DF-qNMR spectrum (typically that of the methyl groups of valine, isoleucine, and leucine between 1.0-1.4 ppm, but could be any resolved peak), $H_S$ is the number of protons contributing to the reference standard peak, $A_S$ is the area of the reference standard peak, $H_P$ is the number of protons contributing to the protein peak, and the various $f$'s are functions that depend on the specific experimental conditions. $f_{DF}$ accounts for attenuation of the protein peak area due to the diffusion filter is derived from the Stejskal-Tanner equation (Johnson, C. S. et al., Concepts in Magnetic Resonance Part A 2012, 40A, 39-65). For the bppste pulse sequence (Pelta, M. D et al., Magn. Reson. Chem. 1998, 36, 706-714) used herein, it is given by $$f_{DF} = 2 \; e^{\frac{\tau_1}{T_1}} \; e^{\frac{\tau_2}{T_2}} \; e^{D \gamma^2 g^2 \delta^2 \left[\Delta - \frac{\delta}{3} - \frac{\tau_2}{2}\right]} \qquad \text{(Eq. 2)}$$

where $\gamma$ is the magnetogyric ratio for $^1$H, g is the pulse-field gradient strength, $\delta$ is the pulse-field gradient length, $\Delta$ is the diffusion delay, $T_1$ is the spin-lattice nuclear relaxation time for the protein's protons of interest, $T_2$ is the spin-spin nuclear relaxation time for the protein's protons of interest, D is the protein's translation diffusion coefficient, $\tau_1$ is the time between the second and third 90° pulses in the bppste pulse sequence (see FIG. 1), $\tau_2$ is the total time between the first and second 90° pulses (and between the third 90° pulse and acquisition) and $\tau_3$ is the total time between the pulse-field gradient pulses of the bipolar-pulse pairs. For the pulse sequence supplied on Agilent instruments, these terms are defined by the following instrument parameters $$\tau_1 = \Delta - \delta - 2t_{gs} - 4\theta_P - 2_{rg} \quad \text{(Eq. 3)}$$

$$\tau_2 = 2(\delta + 2t_{gs} + 2\theta_P + 2t_{rg}) \quad \text{(Eq. 4)}$$

$$\tau_3 = t_{gs} + 2\theta_P + t_{rg} \quad \text{(Eq. 5)}$$

where $t_{gs}$ is the gradient stabilization delay, $t_{rg}$ is the receiver gating time preceding the pulse, and $\Theta$ is the 90° pulse width. For other diffusion pulse sequences, the expression for $f_{DF}$ will be different. $f_{ER}$ contains the instrument parameters necessary for external referencing. In the most basic form $$f_{ER} = \frac{S_S}{S_P} \frac{G_S}{G_P} \quad \text{(Eq. 6)}$$

where S and G are the number of scans and the receiver gain, respectively, used to collect the individual NMR spectra of the protein and reference standard. When using the PUL-CON methodology, it becomes $$f_{ER} = \frac{T_P}{T_S} \frac{\theta_P}{\theta_S} \frac{S_S}{S_P} \frac{G_S}{G_P} \quad \text{(Eq. 7)}$$

where T is the sample temperature during the acquisition of the NMR spectra. $f_{DIL}$ account for dilution of initial protein sample to that of the final NMR sample. If the final volume is obtained volumetrically, and the aliquot of the initial sample is done gravimetrically, then this factor is given by $$f_{DIL} = \frac{\text{vol}_F}{\text{wt}_I} d_I \quad \text{(Eq. 8)}$$

where $\text{vol}_F$ is the volume of final solution (i.e., the NMR sample solution), and $\text{wt}_I$ and $d_I$ are the weight and density of the aliquot of the initial protein solution. Alternatively, if dilution is done by gravimetric addition of both the initial protein solution and $D_2O$, then $$f_{DIL} = 1 + \frac{\text{wt}_{D2O} \cdot d_I}{d_{D2O} \cdot \text{wt}} \quad \text{(Eq. 9)}$$

where $\text{wt}_{D2O}$ and $d_{D2O}$ are the weight and density of $D_2O$. Finally, $f_U$ converts the concentration units from those of the quantitation reference standard, usually millimolar, into the typical units of grams per liter (or equivalently, milligrams per milliliter). In this case $$f_U = \frac{M_P}{1000} \quad \text{(Eq. 10)}$$

where $M_P$ is the molecular weight of the protein.

The first exponential term in the Eq. 2 describes signal attenuation due to $T_1$ nuclear relaxation, the second due to $T_2$ nuclear relaxation, and the third due to molecular diffusion. Of all the terms in the equation, these three quantities ($T_1$, $T_2$, and D) are the only unknowns; all others are pulse sequence/instrument parameters or a physical constant ($\gamma$). $T_1$, $T_2$, and D depend on the molecule and solution conditions, and must be measured for each unique sample. This can be done with three separate experiments using the same pulse sequence as the diffusion filter. Measuring D is a well-known experiment, in which multiple spectra are acquired with increasing gradient strength (Stejskal, E. O. and Tanner, J. E., J. Chem. Phys., 1965, 42, 288-292). This keeps the $T_1$ and $T_2$ terms of Eq 2 constant, making signal attenuation governed solely by D. D is then calculated by applying a suitable algorithm, such as DECRA (Windig, W.; Antalek, B. Chemom. Intell. Lab. Syst., 1997, 37, 241-254). To measure $T_1$ with the Agilent bppste pulse sequence, multiple spectra are acquired using combinations of the diffusion delay and gradient strength (gzlvl1), such that $$gzlvl1_n = gzlvl1_1 \times \sqrt{\frac{\Delta'_1}{\Delta'_n}} \quad \text{(Eq. 11)}$$

where $\Delta'$ is the correct diffusion delay given by $$\Delta' = \Delta - \frac{\delta}{3} - \frac{\tau_3}{2} \quad \text{(Eq. 12)}$$

This keeps the $T_2$ and D terms of Eq 2 constant, making signal attenuation governed solely by $T_1$ relaxation. The effective $T_1$ for the protons of the selected protein peak are then calculated from a mono-exponential fit of $A_P$ VS. $\tau_1$. To measure $T_2$ with the Agilent bppste pulse sequence, multiple spectra are acquired with combinations of the gradient stabilization delay, diffusion delay, and gradient strength, such that $$\Delta_n = \Delta_1 + (t_{rgn} - t_{rg1}) \quad \text{(Eq. 13)}$$

and $gzlvl1_n$ is determined as shown above. This keeps the $T_1$ and D portions of the equation constant, making signal attenuation governed solely by $T_2$ relaxation. The effective $T_2$ for the protons of the selected protein peak can be calculated from a mono-exponential fit of $A_P$ VS. $\tau_2$.

Method A Data Acquisition

An Agilent DD2 600 MHz NMR spectrometer is equipped with an Agilent $^1H$-$^{19}F$/$^{15}N$-$^{31}P$ PFG OneProbe. The probe temperature and pulse-field gradients are calibrated with samples of ethylene glycol and 1% $H_2O$ in $D_2O$, respectively. The NMR spectrum is acquired at 30.0° C. with the bipolar-pulse pair stimulated echo (bppste) pulse sequence. The number of scans is 64. Acquisition parameters include a 20 ppm spectral width, a 1.363 s acquisition time, a 30 s relaxation delay, a 150 ms diffusion delay, 1.4 ms gradient pulses that are 0.569 T/m strong (92% of maximum), and a 1 ms gradient stabilization delay.

To measure the translation diffusion coefficient (D), acquisition parameters include a 1 s relaxation delay, a 200 ms diffusion delay, a 2.0 ms diffusion gradient length, a 0.5 ms gradient stabilization delay, and seven values of the gradient strength ranging from 0.228 to 0.569 T/m (ca. 37-92% of maximum) with logarithmic spacing. The spin-lattice nuclear relaxation time ($T_1$) is measured with the bppste pulse sequence using a 20 ppm spectral width, a 1.363 s acquisition time, a 3.637 s relaxation delay, a 2.0 ms diffusion gradient length, and a 0.5 ms gradient stabilization delay. Five pairs of the diffusion delay and gradient strength- (100 ms, 0.569 T/m); (203 ms, 0.400 T/m); (408 ms, 0.281 T/m); (804 ms, 0.200 T/m); and (1202 ms, 0.164 T/m)—are used.

The spin-spin nuclear relaxation time ($T_2$) is also measured with the bppste pulse sequence using a 20 ppm spectral width, a 1.363 s acquisition time, a 1 s relaxation delay, a 1.4 ms diffusion gradient length. Six sets of the gradient stabilization delay, diffusion delay, and gradient strength are used-(1 ms, 150.001 ms, 0.570); (2 ms, 150.002 ms, 0.571 T/m); (4 ms, 150.004 ms, 0.573 T/m); (8 ms, 150.008 ms, 0.577 T/m); (12 ms, 150.012 ms, 0.581 T/m); and (16 ms, 150.016 ms, 0.575 T/m).

Data Analysis

The DF-qNMR, $T_1$, and $T_2$ data are processed in MNova v 11.0 (Mestrelab Research, S. L., Santiago de Compostela, Spain), and the diffusion data are processed and analyzed with DOSYToolbox v2.5 (Nilsson, M. J. Magn. Reson. 2009, 200, 296-302). The FIDs are zero-filled one time and multiplied by an exponential window function of 2.93 Hz prior to Fourier transform. The diffusion coefficients are obtained using the DECRA algorithm available in DOSYToolbox. The values of $T_1$ and $T_2$ are calculated from the bppste pulse sequence by regression analysis using MATLAB 2016b (MathWorks, Inc., Natick, Ma). The peak areas of the leucine, isoleucine, and/or valine methyls are obtained by deconvolution using the line fitting routine in MNova or CRAFT.

Using Method A on NIST Antibody RM 8761

Figure 2:
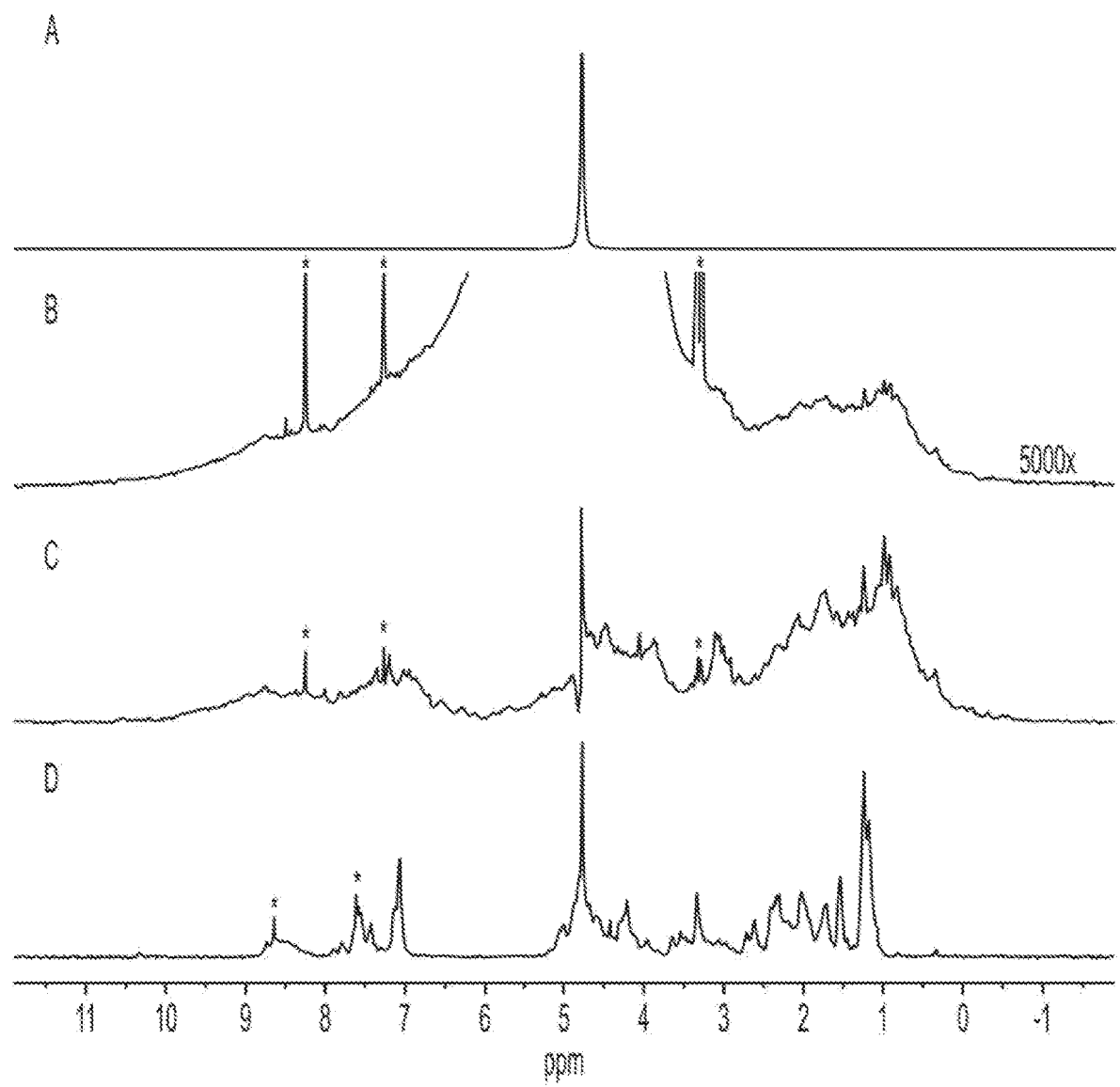
FIG. 2. $^1$H NMR spectra of NIST mAb. $^1$H NMR spectrum of NIST mAb (A) in native form with a standard one-pulse sequence, (B) same as A with vertical scale 5000×, (C) native with a diffusion-filter, and (D) denatured with a diffusion filter. Peaks marked with an asterisk are from the histidine buffer. The number of scans was 1024 for A-C and 64 for D.

To illustrate the challenges of quantitating large, formulated proteins by NMR, a sample of NIST RM 8761 (10 g/L antibody, 12.5 mM L-histidine HCl, pH 6.0, commercially available from the National Institute of Standards and Technology (NIST); see e.g., Schiel et al., Anal. and Bioanal. Chem., 410 (8): 2127-2139 (2018)) is treated with 10% $D_2O$ and the $^1H$ 1D NMR spectrum is obtained (FIG. 2). The water signal is so intense and broad that it obscures the signals of the antibody. The histidine excipient peaks are also observed in the spectrum. To get a viable spectrum of the protein, these dominant peaks must be eliminated. One NMR technique that is is ideal for this application is a "diffusion filter", where peaks are eliminated from the spectrum based on the diffusion coefficients, and hence size, of the corresponding molecules. The $^1H$-NMR spectrum acquired on the same NIST mAb sample with the bipolar-pulse pair stimulated echo (bppste) diffusion pulse sequence as a diffusion filter is also shown in FIG. 2. The diffusion filter is effective at removing the unwanted signals of the formulation without introducing baseline artifacts or phase distortions.

However, in most cases, there is insufficient resolution for accurate peak identification and integration due to the characteristic broad linewidths of the protein resonances. This is primarily due to the higher-order structure (HOS) of the protein. A single type of amino acid, which would otherwise have very similar chemical shifts, shows a wide chemical shift distribution due to the unique magnetic environments resulting from the secondary, tertiary, and quaternary structure of the protein. Therefore, the HOS is removed by denaturing the protein. Adding denaturant to the protein solution causes the volume of the sample to expand. To be truly quantitative, more solvent is added achieve a precise volume, for example using a volumetric flask. This is the basis for $f_{DIL}$ in Eq 1.

The diffusion-filtered $^1H$-NMR of NIST RM 8761 sample prepared with 6 M guanidinium chloride-do is shown in FIG. 2. Decrease in linewidth and subsequent increase in signal-to-noise is observed. The groups of peaks between 1.0-1.4 ppm, which correspond to the methyl groups of isoleucine, leucine, and/or valine has near-baseline resolution, enabling it to be integrated for quantitative analysis.

The diffusion filter is effective at isolating the protein signals from the matrix; however, the diffusion filter results in a lack of inherent quantitation of the measured NMR peak areas. Routine qNMR experiments use a simple NMR pulse sequence, which consists of three basic elements: a nuclear-relaxation delay, one radio-frequency pulse, and a data-acquisition period. When a sufficiently long nuclear relaxation delay is used, the resulting NMR peak area is accurately and reproducibly proportional to the number of observed nuclei; thus, the experiment is quantitative. All other NMR pulse sequences, including the diffusion sequence employed here, require multiple radiofrequency pulses separated by various delays. Consequently, the resulting spectra are no longer intrinsically quantitative due to factors that attenuate the peaks from the equilibrium value. However, if those factors are known and the extent of attenuation can be calculated, then the diffusion filter can be made quantitative. This is the basis for $f_{DF}$ in Eq 1.

An external reference standard is preferred over an internal reference standard because the former avoids potential interactions between the two molecules and/or overlap of the peaks in the NMR spectrum, although an internal standard can be used. Several external standard methods have been reported, including the PULCON technique (e.g., pulse length-base concentration determination). This technique correlates the absolute areas from two individual spectra, one of the reference standard and the other of the analyte, even if the solution conditions and experimental parameters are different. Therefore, the external reference standard does not need to have similar characteristics to the analyte of interest or even be a protein. Furthermore, rather than needing a standard for every amino acid, as is the case for AAA, this method only requires a single standard.

Figure 3A:
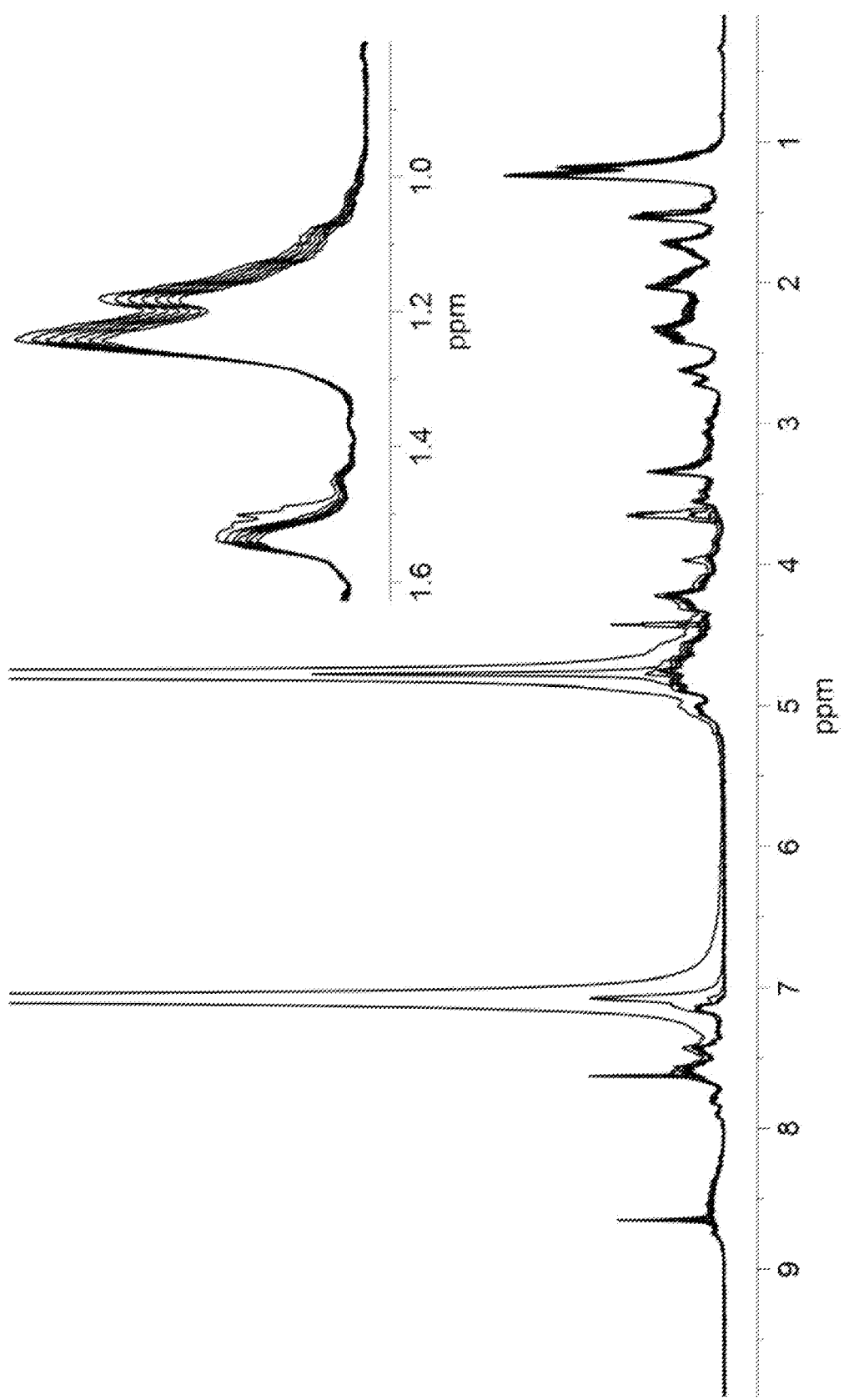
FIGS. 3A-3B. D measurements on NIST mAb.
Figure 3B:
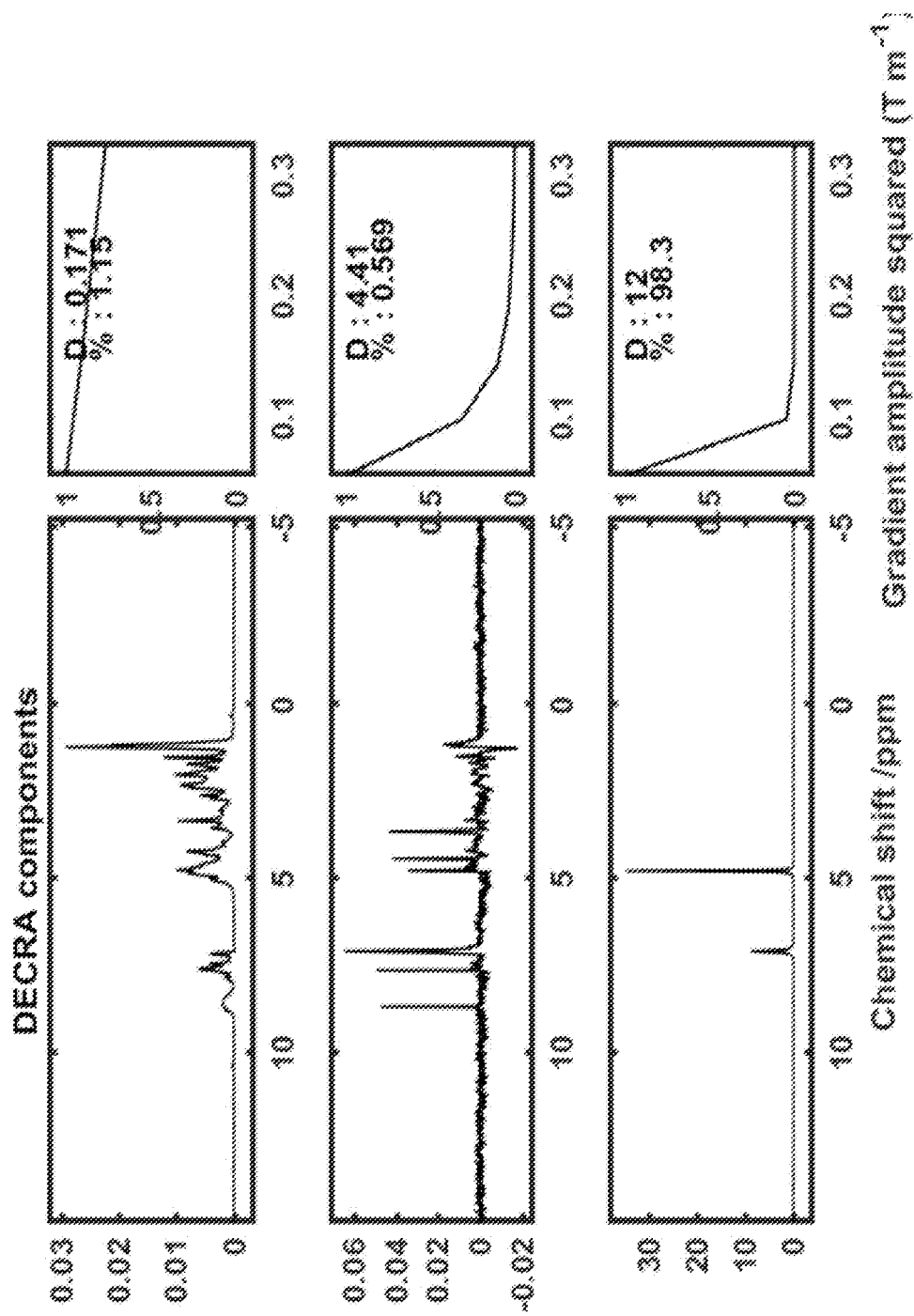
Figure 4A:
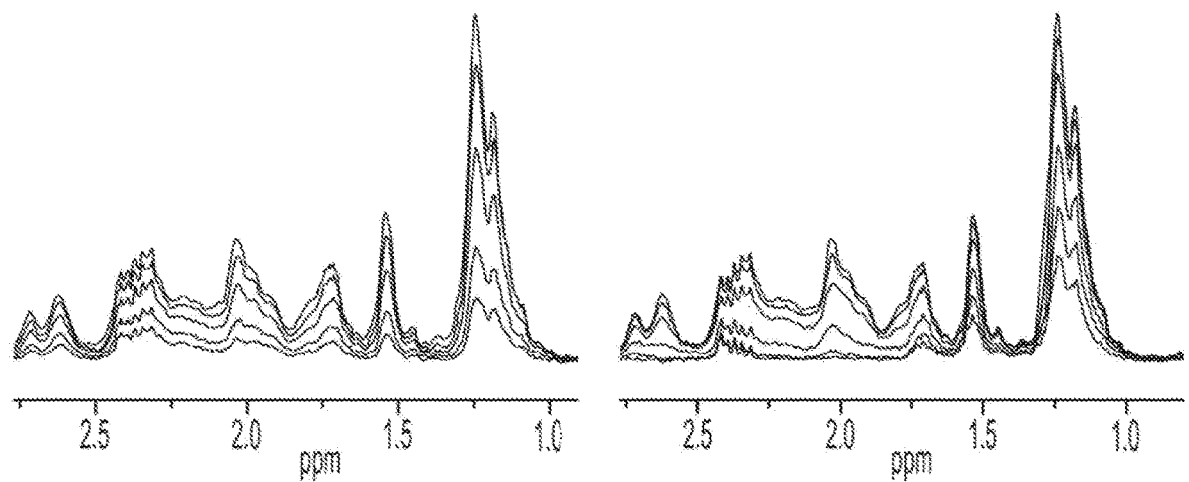
FIGS. 4A-4B. $T_1$ and $T_2$ measurements on NIST mAb.
Figure 4B:
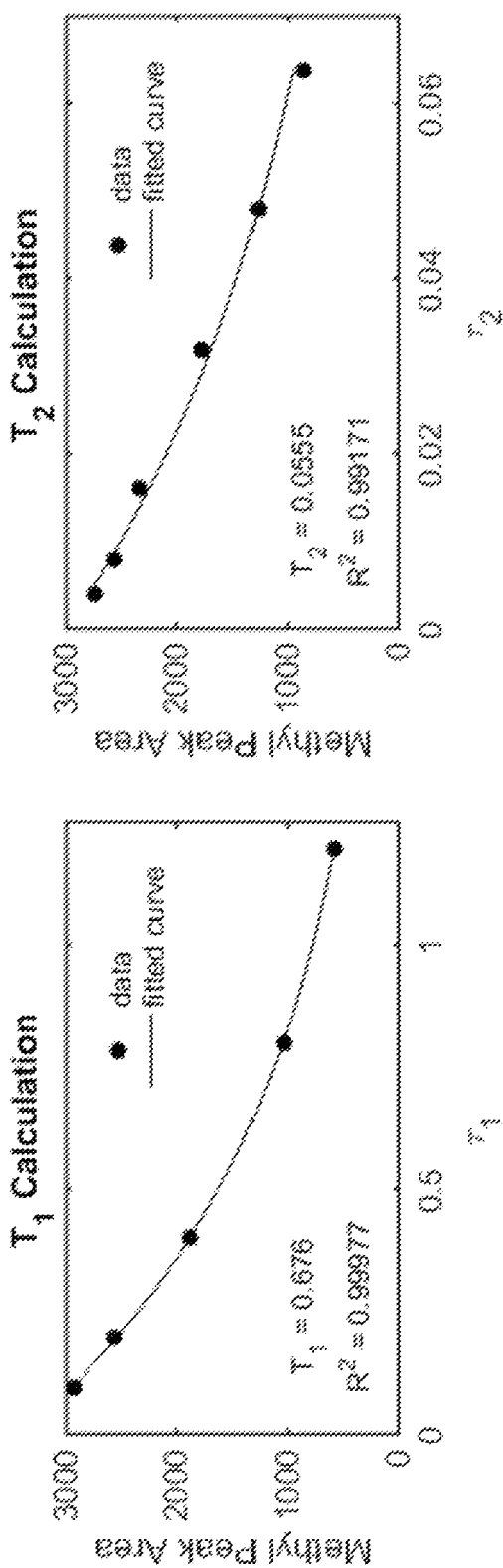

To demonstrate the accuracy and precision of Method A, three independent replicates of the NIST RM 8761 sample are evaluated. Ample signal-to-noise is obtained on this 10 g/L protein formulation using only 64 scans and a 37-min total acquisition time. The group of signals for the methyl groups of I/L/V in the protein (1.0-1.4 ppm), which corresponds to 1,476 protons, has near baseline resolution. These results enable accurate integration for quantitation. To facilitate the concentration calculation, $T_1$, $T_2$, and D are also measured for this peak group with the bppste pulse sequence as described above, data acquisition and analysis performed are shown in FIG. 3 and FIG. 4.

The total experiment time for all four NMR experiments on one replicate is 110 min. The concentration of each replicate is then calculated from Eq. 9 using the intact, non-glycosylated molecular weight (148,041 Da) and a dilution factor based on the weight of the aliquot and the measured sample density. The average concentration is determined to be 10.02 g/L with an RSD of 0.55%. This is in agreement with the labeled value of 10 g/L.

These data demonstrate that Method A can be used to accurately and precisely determine the concentration of an antibody.

Using Method A on NIST Bovine Serum Albumin (BSA)

Figure 5:
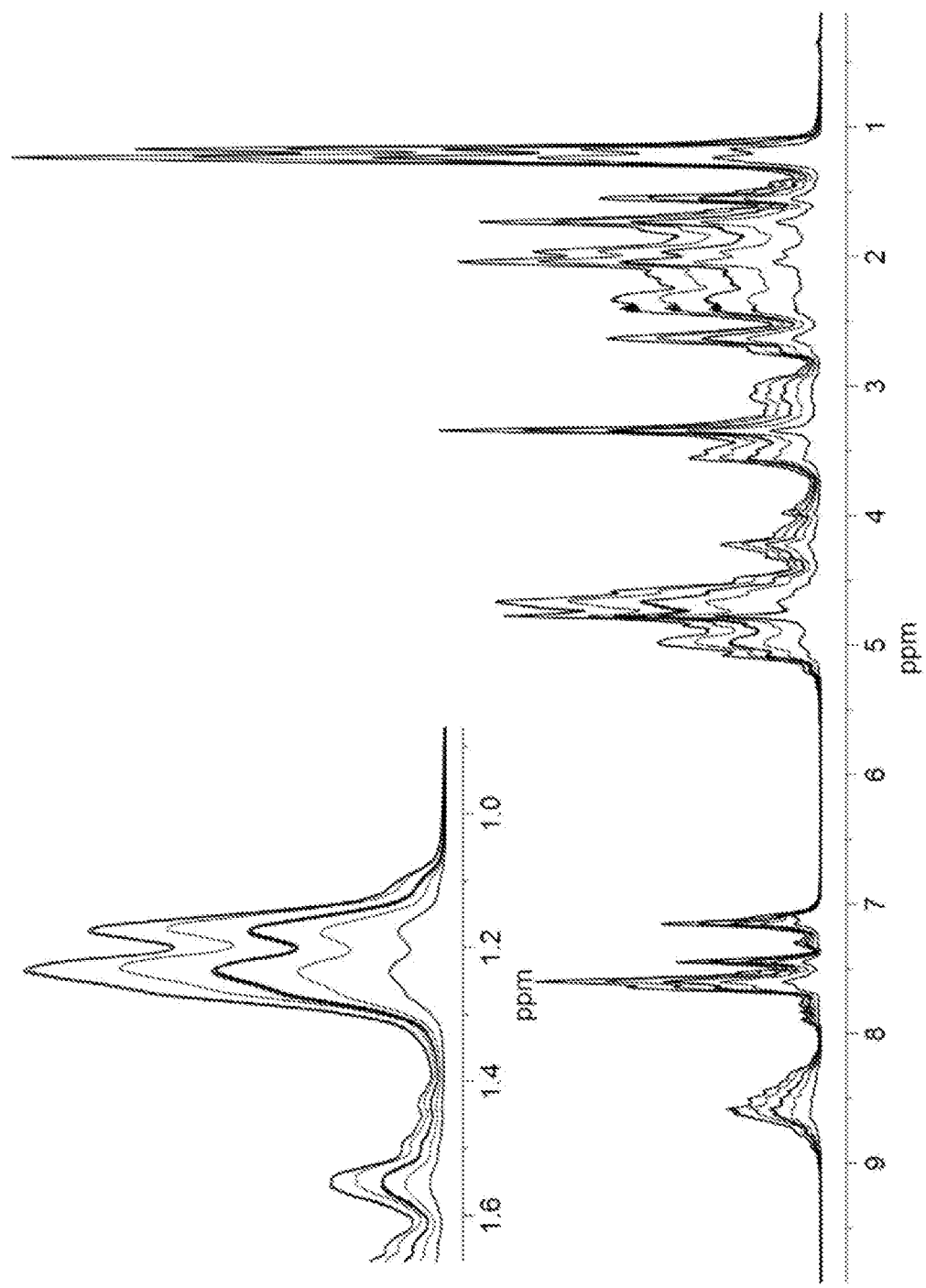
FIG. 5. DF-qNMR spectra of the 14 samples of denatured NIST BSA. Inset: magnified image of indicated region.

NIST (BSA) standard reference material 927e (67.38 g/L, 20 mM sodium chloride, pH adjusted to 6.5-6.8 with 1.0 mol/L sodium hydroxide, commercially available from the National Institute of Standards and Technology) is gravimetrically diluted to four additional protein concentrations (Table 1, samples B1-B4). Fourteen total samples are analyzed, including six replicates at the middle concentration (B3), three replicates at each of the highest (B5) and lowest (B1) concentrations, and single replicates at the intermediate concentrations (B2 and B4). The NMR sample for each replicate is prepared as described above. The Method A data acquisition and analysis are performed as described above. The resulting fourteen DF-qNMR spectra are shown superimposed in FIG. 5.

These data demonstrate that the peak from water has been almost eliminated, the baseline is unperturbed, and the group of signals for the methyl groups of I/L/V in the protein has near baseline resolution. The concentration for each sample is calculated from Eq. 1 using a molecular weight of 66,398 Da and reported in Table 1. For all five concentrations, the value measured by Method A is similar to the value calculated from gravimetric dilution. As shown below in Table 1, the RSD is less than 1% for all three sets of replicates.

TABLE 1

Results for the NIST BSA Samples.

| Sample | Method A Conc. (g/L) | RSD | Gravimetric Conc. (g/L) | Difference |
|---|---|---|---|---|
| B1 | 9.297 | 0.61% | 9.525 | 2.39% |
| B2 | 23.90 | — | 23.91 | 0.04% |
| B3 | 37.53 | 0.81% | 38.11 | 1.54% |
| B4 | 52.50 | — | 52.82 | 0.60% |
| B5 | 66.18 | 0.82% | 67.38 | 1.78% |

Figure 6:
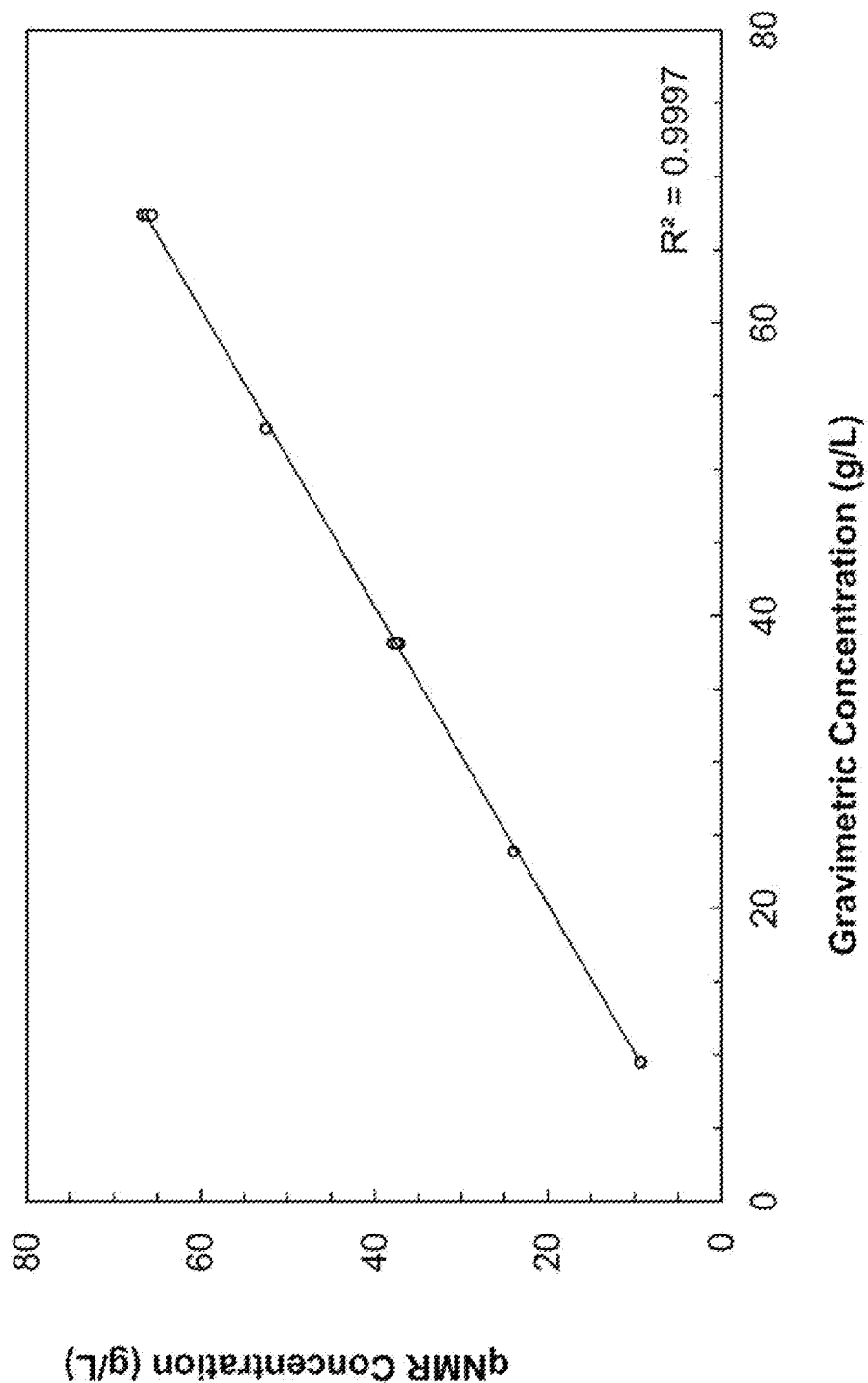
FIG. 6. NIST BSA sample concentrations: Method A versus gravimetric measurement.

As shown in FIG. 6, a plot of the Method A concentrations vs the gravimetric concentrations yielded a regression line with $R^2=0.9997$, indicating linearity across the concentration range examined.

These data demonstrate that Method A can be used to accurately and precisely determine the concentration of a medium-size protein across a wide concentration range.

Figure 7:
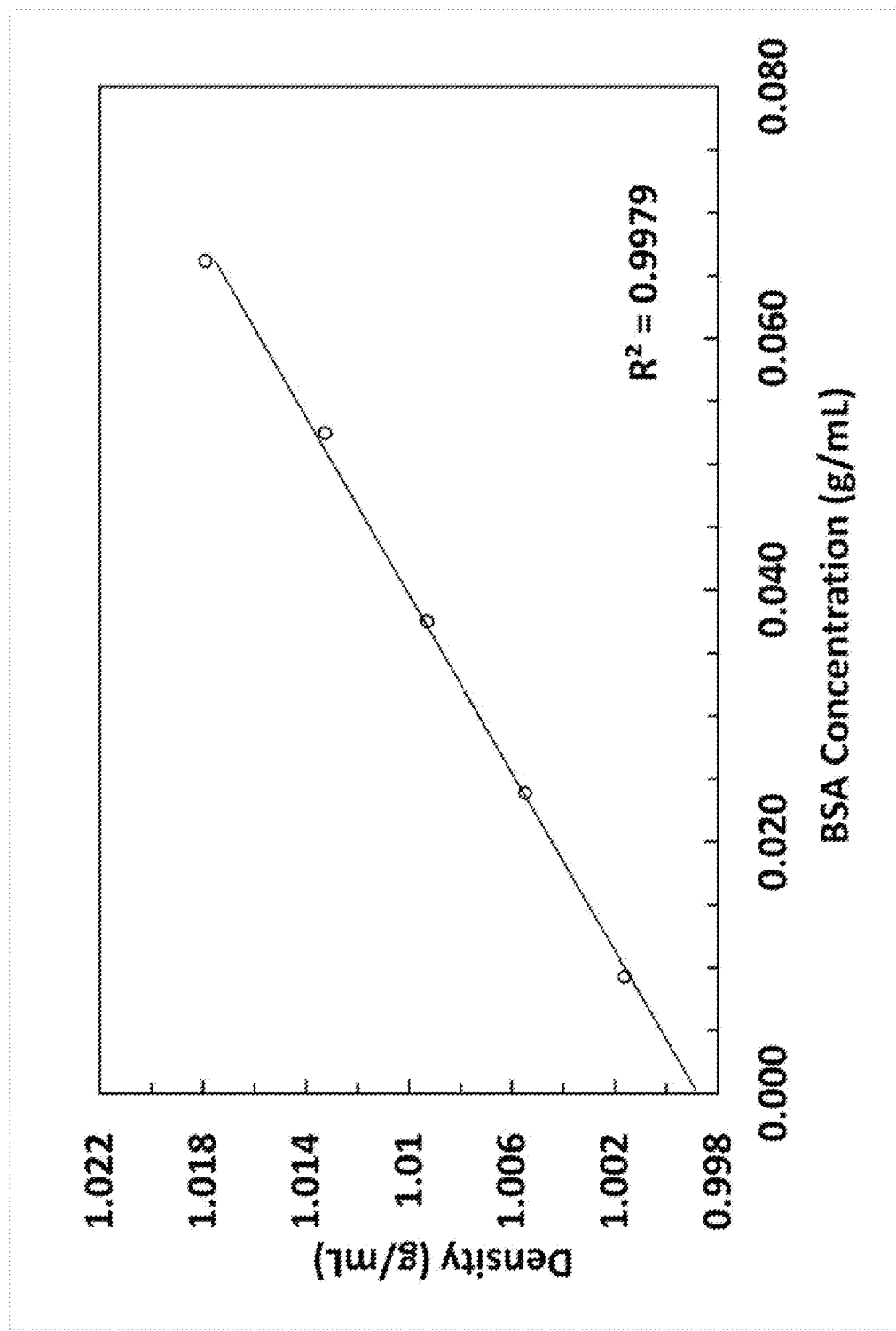
FIG. 7. NIST BSA Partial-Specific Volume: sample density versus BSA concentration.

FIG. 7 demonstrates a plot of the sample density as a function of the protein concentration, as determined by Method A. The equation that relates the two quantities is $\rho=\rho_0+(1-\bar{v}\rho_0)(c/1000)$, as defined above. The slope of the regression line yields the partial-specific volume ($\bar{v}$) of BSA, which was found to be 0.718 mL/g.

Using Method A on a Bispecific Antibody

Samples of a bispecific antibody (given by the sequences in Table 1 of U.S. Pat. No. 9,718,884), with five different concentrations and 14 total samples, are prepared as described above. Method A data acquisition and analysis are performed as described above. According to the procedures essentially described above, the following data were obtained.

Figure 8:
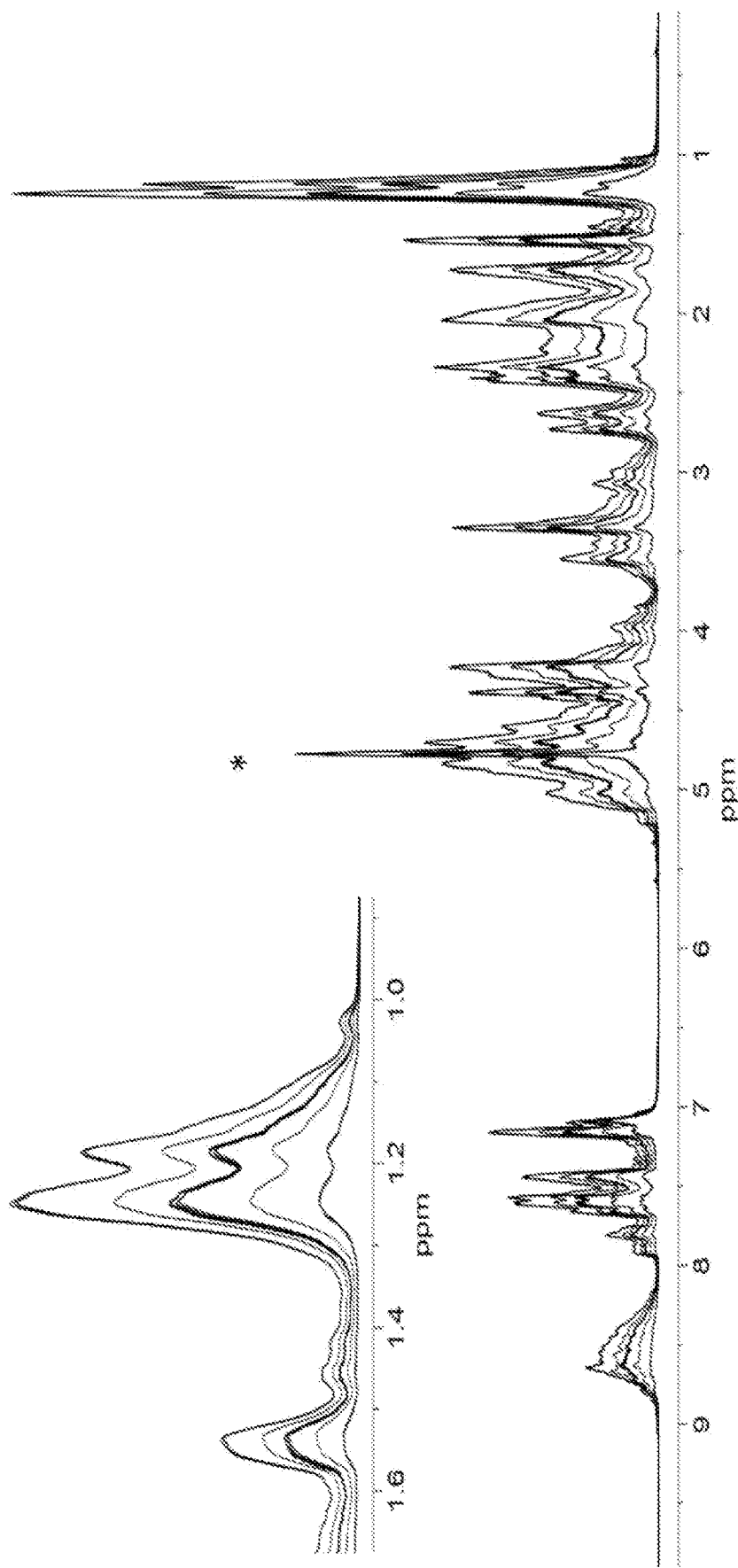
FIG. 8. DF-qNMR spectra of the 14 samples of denatured bispecific antibody. DF-qNMR spectra of the 14 samples of the denatured bispecific antibody. The peak for residual water is marked with an asterisk. Inset: magnified image of indicated region.

FIG. 8 shows the resulting DF-qNMR spectra, which are similar in overall appearance and quality to those of BSA (shown above). The concentrations were calculated with Eq. 1, using the theoretical molecular weight of the intact, non-glycosylated protein (~200,000 Da), and summarized in Table 2 below.

TABLE 2

Results for the bispecific antibody.

| Sample | Method A Conc. (g/L) | RSD | Estimated Conc. (g/L) | Difference |
|---|---|---|---|---|
| C1 | 9.427 | 0.25% | 9.277 | −1.61% |
| C2 | 24.59 | — | 24.61 | 0.09% |
| C3 | 41.62 | 1.25% | 39.67 | −4.92% |
| C4 | 54.43 | — | 55.02 | 1.07% |
| C5 | 78.37 | 0.85% | 74.01 | −5.89% |

Figure 9:
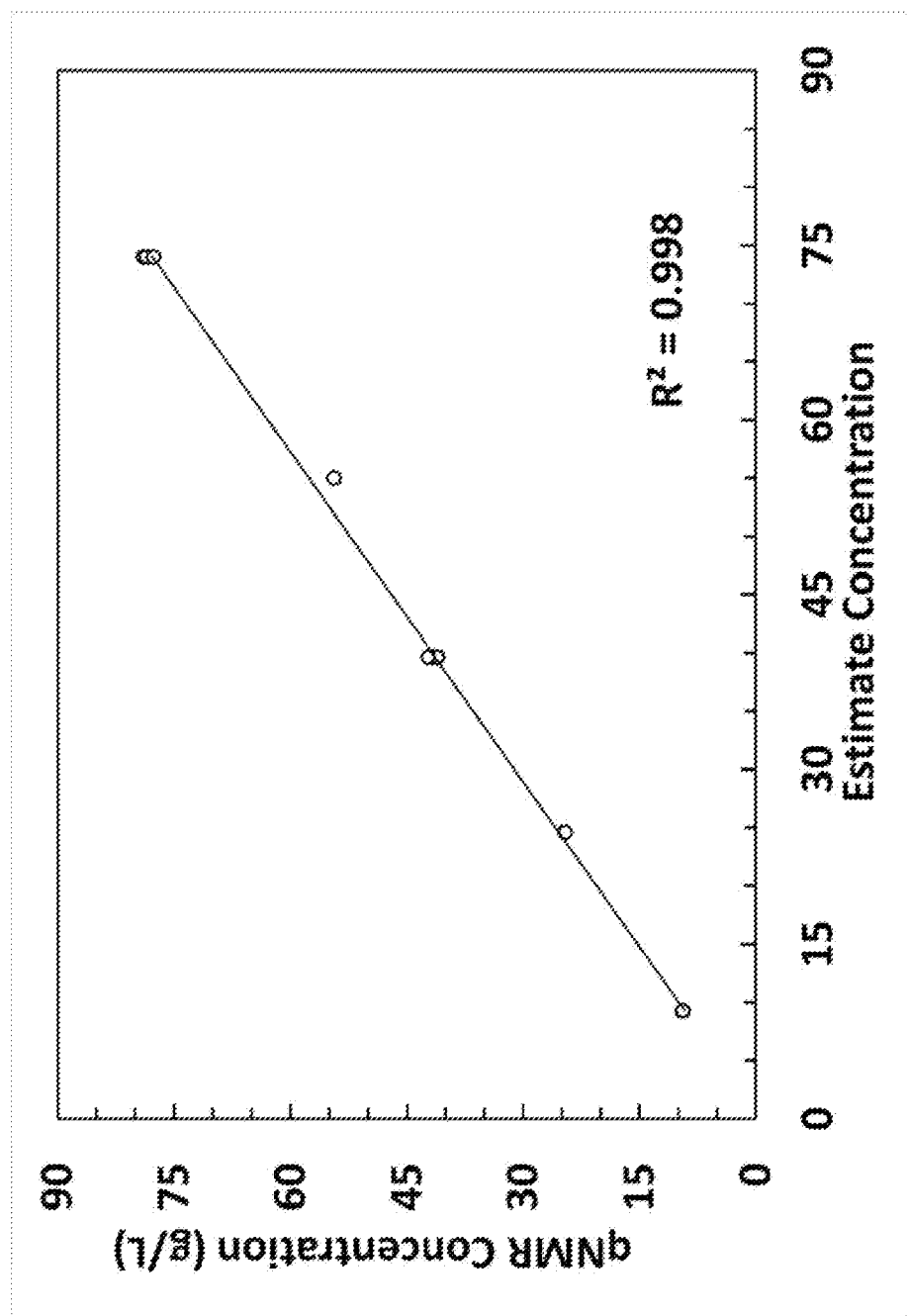
FIG. 9. Bispecific antibody sample concentrations: Method A versus gravimetric measurement.

As shown in FIG. 9, a plot of the Method A concentrations versus the gravimetric concentrations yielded a regression line with $R^2=0.996$.

These data demonstrate that Method A can be used to determine the concentration of a bispecific antibody across a very wide concentration range.

Using Method A on a ~5000 Da Peptide

Samples of a dilute, small peptide (ca. 5,000 Da; given by the sequence in Example 4 of PCT/US2017/041922) are prepared with and without chaotropic agent as described above. The lower concentration of denaturant (2 M) is acceptable since the peptide exists natively as a random coil and the concentration is low. Basic conditions are required for sample stability; therefore, urea-d4 is used. The Method A data acquisition and analysis are performed as described above with the exception that there were 624 scans for each acquisition instead of 64 scans. Following procedures essentially as described above, the following data were obtained. A slight phase distortion was observed for the residual water signal, but this did not hinder data analysis. Addition of the chaotropic agent produced better water suppression, sharper peaks and subsequently more resolution and sensitivity. The concentration of each replicate was calculated from Eq. 1. The average total protein concentration was determined to be 0.65 g/L with an RSD of 3.6%. This was similar to the value obtained by mass balance (0.63 g/L). These data demonstrate that Method A can be used for a dilute sample of a small peptide.

ILLUSTRATIVE EMBODIMENTS

The following comprises a list of illustrative embodiments according to the instant disclosure which represent various embodiments of the instant disclosure.

These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method of determining the concentration of a protein or peptide in solution, wherein the method comprises:
   (i) denaturing the protein or optionally denaturing the peptide;
   (ii) performing qNMR spectroscopy with a diffusion filter; and
   (iii) calculating the concentration of the protein or peptide using a reference standard and a referencing technique.
2. The method of embodiment 1, wherein the peptide is denatured.
3. The method of embodiment 1 or embodiment 2, wherein the protein or peptide is denatured with a chaotropic agent.

4. The method of embodiment 3, wherein the chaotropic agent is guanidinium chloride-$d_6$ or urea-$d_4$.
5. The method of any one of embodiments 1-4, wherein the reference standard is an external reference standard.
6. The method of embodiment 5, wherein the external reference standard is a small-molecule primary standard.
7. The method of embodiment 5, wherein the external reference standard is maleic acid.
8. The method of any one of embodiments 1-7, wherein the solution comprises $D_2O$.
9. The method of any one of embodiments 1-8, wherein the referencing technique is PULCON.
10. The method of any one of embodiments 1-9, wherein the protein is an antibody.
11. The method of embodiment 10, wherein the antibody is a monoclonal antibody.
12. The method of embodiment 10, wherein the antibody is a bispecific antibody.
13. A method of determining a molecular parameter of a protein or peptide in solution, wherein the method comprises:
    (i) denaturing the protein or optionally denaturing the peptide;
    (ii) performing qNMR spectroscopy with a diffusion filter;
    (iii) calculating the concentration of the protein or peptide using a reference standard and a referencing technique; and
    (iv) determining the molecular parameter of the protein or peptide from the calculated concentration.
14. The method of embodiment 13, wherein the peptide is denatured.
15. The method of embodiment 13 or embodiment 14, wherein the molecular parameter is the extinction coefficient.
16. The method of embodiment 15, wherein the extinction coefficient is determined by the Beer-Lambert Law.
17. The method of any one of embodiments 13-16, wherein the protein or peptide is denatured with a chaotropic agent.
18. The method of embodiment 17, wherein the chaotropic agent is guanidinium chloride-$d_6$ or urea-$d_4$.
19. The method of any one of embodiments 13-18, wherein the reference standard is an external reference standard.
20. The method of embodiment 19, wherein the external reference standard is a small-molecule primary standard or maleic acid.
21. The method of embodiment 20, wherein the external reference standard is a small-molecule primary standard.
22. The method of embodiment 20, wherein the external reference standard is maleic acid.
23. The method of any one of embodiments 13-22, wherein the solution comprises $D_2O$.
24. The method of any one of embodiments 13-23, wherein the referencing technique is PULCON.
25. The method of any one of embodiments 13, 15-24, wherein the protein is an antibody.
26. The method of embodiment 25, wherein the antibody is a monoclonal antibody.
27. The method of embodiment 25, wherein the antibody is a bispecific antibody.
28. A method of determining a molecular parameter of a protein or peptide in a reference batch, wherein the method comprises:
    a. denaturing the protein or optionally denaturing the peptide;
    b. performing qNMR spectroscopy with a diffusion filter;
    c. calculating the concentration of the protein or peptide using a reference standard and a referencing technique; and
    d. determining the molecular parameter of the protein or peptide from the calculated concentration.
29. The method of claim 28, further comprising determining the concentration of the protein or peptide in a test batch, wherein said concentration of peptide or protein in the test batch is determined from the molecular parameter.
30. The method of embodiment 28 or embodiment 29, wherein the molecular parameter is the extinction coefficient.
31. The method of embodiment 30, wherein the extinction coefficient is determined by the Beer-Lambert law.
32. The method of any one of embodiments 28-31, wherein the peptide is denatured.
33. The method of any one of embodiments 28-32, wherein the protein or peptide is denatured with a chaotropic agent.
34. The method of embodiment 33, wherein the chaotropic agent is guanidinium chloride-$d_6$ or urea-$d_4$.
35. The method of any one of embodiments 28-34, wherein the reference standard is an external reference standard.
36. The method of embodiment 35, wherein the external reference standard is a small-molecule primary standard.
37. The method of embodiment 35, wherein the external reference standard is maleic acid.
38. The method of any one of embodiments 28-37, wherein the solution comprises $D_2O$.
39. The method of any one of embodiments 28-38, wherein the referencing technique is PULCON.
40. The method of any one of embodiments 28-31, 33-39 wherein the protein is an antibody.
41. The method of embodiment 40, wherein the antibody is a monoclonal antibody.
42. The method of embodiment 40, wherein the antibody is a bispecific antibody.
43. The method of any one of embodiments 13-42, wherein the method further comprises using the molecular parameter to determine the concentration of the protein or peptide in formulating the protein or peptide.
44. The method of any one of embodiments 13-42, wherein the method further comprises using the molecular parameter to determine the concentration of the protein or peptide in a test at lot release.
45. The method of embodiment 44, wherein the test at lot release is a UV test at lot release.
46. The method of any one of embodiments 13-42, wherein the method further comprises using the molecular parameter to determine the concentration of the protein or peptide in the preparation of a lot.
47. The method of any one of embodiments 13-42, wherein the method further comprises using the molecular parameter to determine the concentration of the protein or peptide in determining a dose of the protein or peptide.
48. The method of any one of embodiments 13-42, wherein the method further comprises using the molecular parameter to determine the concentration of the protein or peptide during manufacturing.

49. The method of any one of embodiments 1-48, wherein the protein or peptide is the active ingredient in dulaglutide, ixekizumab, ramucirumab, cetuximab, olaratumab, necitumumab, galcanezumab, or mirikizumab.

We claim:

1. A method of determining absolute protein concentration of a protein in a drug substance or a drug product solution, wherein the drug substance or drug product contains a single protein, comprising the steps of:
   a. denaturing the protein, wherein the denaturing causes the protein to become unfolded and lose a majority of its secondary, tertiary, and quaternary structural features;
   b. performing qNMR spectroscopy on the denatured protein, wherein said step of performing qNMR spectroscopy includes use of a diffusion filter; and
   c. calculating the absolute protein concentration of the protein using a reference standard and a referencing technique.

2. The method of claim 1, further comprising the step of:
   d. determining a molecular parameter of the protein using the calculated concentration of the protein and a measured property of the drug substance or the drug product solution.

3. The method of claim 2, wherein the molecular parameter of the protein comprises extinction coefficient, refractive index, or partial specific volume.

4. The method of claim 3, wherein the extinction coefficient is determined by the Beer-Lambert Law.

5. The method of claim 2, wherein the molecular parameter is that of a protein in a reference batch.

6. The method of claim 5, wherein the molecular parameter of the protein in the reference batch is used to determine the absolute protein concentration of the protein in a test batch.

7. The method of claim 2, wherein the method further comprises using the molecular parameter to determine the protein concentration of the protein in a test batch.

8. The method of claim 2, wherein said step of determining the molecular parameter further comprises measuring a property of the drug substance or the drug product solution using ultraviolet spectroscopy.

9. The method of claim 1 wherein the protein is denatured with a chaotropic agent.

10. The method of claim 9, wherein the chaotropic agent is guanidinium chloride-$d_6$ or urea-$d_4$.

11. The method of claim 1, wherein the reference standard is an external reference standard.

12. The method of claim 11, wherein the external reference standard is a small-molecule primary standard.

13. The method of claim 11, wherein the external reference standard is maleic acid.

14. The method of claim 1, wherein the solution comprises $D_2O$.

15. The method of claim 1, wherein the referencing technique is PULCON.

16. The method of claim 1, wherein the protein is an antibody.

17. The method of claim 16, wherein the antibody is a monoclonal antibody, a bispecific antibody, a trispecific antibody, or a tetra-specific antibody.

18. The method of claim 1, wherein the protein is a fusion protein.

19. The method of claim 1, wherein the protein is a peptide.

* * * * *